(12) United States Patent
Fava et al.

(10) Patent No.: US 8,425,767 B2
(45) Date of Patent: Apr. 23, 2013

(54) DEVICE FOR CONNECTING TO A LIQUID SOURCE

(75) Inventors: Massimo Fava, Mirandola (IT); Salvatore Rinaldi, Bolognetta (IT)

(73) Assignee: Gambro Lundia AB, Lund (SE)

( * ) Notice: Subject to any disclaimer, the term of this patent is extended or adjusted under 35 U.S.C. 154(b) by 554 days.

(21) Appl. No.: 12/601,191

(22) PCT Filed: May 25, 2007

(86) PCT No.: PCT/IB2007/001372
§ 371 (c)(1),
(2), (4) Date: Mar. 2, 2010

(87) PCT Pub. No.: WO2008/146068
PCT Pub. Date: Dec. 4, 2008

(65) Prior Publication Data
US 2010/0181235 A1    Jul. 22, 2010

(51) Int. Cl.
*B01D 61/32* (2006.01)
*A61M 1/00* (2006.01)

(52) U.S. Cl.
USPC .............. 210/86; 137/558; 210/90; 210/96.2; 210/103; 210/104; 210/188; 210/257.2; 210/258; 210/321.6; 210/645; 210/646; 804/5.01; 804/31; 804/65

(58) Field of Classification Search ............. 210/85, 210/90, 96.2, 103, 104, 123, 134, 137, 188, 210/257.2, 258, 321.6, 645–647, 86; 604/5.01, 604/6.01, 6.09, 65, 67, 19, 30, 31; 137/551, 137/558
See application file for complete search history.

(56) References Cited

U.S. PATENT DOCUMENTS

| | | | |
|---|---|---|---|
| 3,352,779 A * | 11/1967 | Austin et al. | 210/646 |
| 3,871,913 A | 3/1975 | Shaldon | |
| 3,989,625 A * | 11/1976 | Mason | 210/94 |
| 4,085,046 A | 4/1978 | Saporito, Jr. | |
| 4,103,537 A | 8/1978 | Victor | |
| 4,122,010 A | 10/1978 | Riede et al. | |
| 4,134,834 A | 1/1979 | Brous | |
| 4,153,554 A | 5/1979 | von der Heide et al. | |
| 4,158,034 A | 6/1979 | Riede et al. | |
| 4,166,031 A | 8/1979 | Hardy | |
| 4,332,264 A | 6/1982 | Gortz et al. | |
| 4,444,596 A | 4/1984 | Gortz et al. | |

(Continued)

FOREIGN PATENT DOCUMENTS

| CA | 2310879 A | 12/2000 |
|---|---|---|
| DE | 1927 615 A1 | 12/1970 |

(Continued)

Primary Examiner — Joseph Drodge
(74) Attorney, Agent, or Firm — Pearne & Gordon LLP (57) ABSTRACT

A connecting device comprises a buffer chamber (2), a first connecting line (3) between a liquid source (4) and an inlet (5) of the buffer chamber, a second connecting line (9) between an outlet (10) of the buffer chamber and the medical treatment apparatus (11), two valves (7, 8) arranged in series on the first connecting line, a pump (12) on the second connecting line, two liquid level sensors (15, 16) operating in the buffer chamber, a vent valve (18) connected to the buffer chamber. The liquid source is a centralized distribution plant of dialysate, while the medical treatment apparatus is a dialysis apparatus. The invention prevents back-contamination of the centralized plant with disinfectant sourced from the dialysis apparatus.

22 Claims, 3 Drawing Sheets

U.S. PATENT DOCUMENTS

| | | | |
|---|---|---|---|
| 4,508,622 A | 4/1985 | Polaschegg et al. | |
| 4,602,249 A | 7/1986 | Abbott | |
| 4,606,826 A | 8/1986 | Sano et al. | |
| 4,695,385 A | 9/1987 | Boag | |
| 4,715,398 A | 12/1987 | Shouldice et al. | |
| 4,728,496 A | 3/1988 | Petersen et al. | |
| 4,734,198 A | 3/1988 | Harm et al. | |
| 4,789,467 A | 12/1988 | Lindsay et al. | |
| 4,804,369 A | 2/1989 | Lapeyre et al. | |
| 4,857,181 A | 8/1989 | Shouldice et al. | |
| 5,015,389 A | 5/1991 | Portillo, Jr. | |
| 5,094,748 A | 3/1992 | Portillo, Jr. | |
| 5,110,477 A | 5/1992 | Howard et al. | |
| 5,256,371 A | 10/1993 | Pippert | |
| 5,268,144 A | 12/1993 | Heilmann et al. | |
| 5,304,349 A | 4/1994 | Polaschegg | |
| 5,347,848 A | 9/1994 | Schoeffel et al. | |
| 5,382,232 A * | 1/1995 | Hague et al. | 604/65 |
| 5,603,902 A | 2/1997 | Maltais et al. | |
| 5,616,305 A | 4/1997 | Mathieu | |
| 5,624,551 A | 4/1997 | Baumann et al. | |
| 5,733,457 A | 3/1998 | Hovland et al. | |
| 5,783,072 A | 7/1998 | Kenley et al. | |
| 5,895,578 A | 4/1999 | Simard et al. | |
| 6,044,691 A | 4/2000 | Kenley et al. | |
| 6,235,199 B1 * | 5/2001 | Peterson et al. | 210/646 |
| 6,251,279 B1 | 6/2001 | Peterson et al. | |
| 6,280,632 B1 * | 8/2001 | Polaschegg | 210/739 |
| 6,284,131 B1 | 9/2001 | Hogard et al. | |
| 6,296,762 B1 | 10/2001 | Jonsson et al. | |
| 6,379,617 B1 | 4/2002 | Spickermann | |
| 6,454,736 B1 | 9/2002 | Ludt et al. | |
| 6,537,450 B2 | 3/2003 | Russell et al. | |
| 6,595,944 B2 | 7/2003 | Balschat et al. | |
| 6,649,057 B2 | 11/2003 | Sano | |
| 6,685,831 B2 | 2/2004 | Donig et al. | |
| 6,787,032 B2 | 9/2004 | Kurome et al. | |
| 7,662,139 B2 * | 2/2010 | Demers et al. | 604/415 |
| 2001/0040127 A1 | 11/2001 | Donig et al. | |
| 2002/0008378 A1 | 1/2002 | Smith | |
| 2002/0088752 A1 | 7/2002 | Balschat et al. | |
| 2002/0134721 A1 | 9/2002 | Kurome et al. | |
| 2003/0034305 A1 | 2/2003 | Luchmann et al. | |
| 2003/0080059 A1 | 5/2003 | Peterson et al. | |
| 2004/0195157 A1 | 10/2004 | Mullins et al. | |
| 2004/0262203 A1 | 12/2004 | Nishimura et al. | |
| 2005/0047959 A1 | 3/2005 | Brandl et al. | |
| 2005/0090805 A1 | 4/2005 | Shaw et al. | |

FOREIGN PATENT DOCUMENTS

| | | |
|---|---|---|
| DE | 34 42 744 A1 | 6/1986 |
| DE | 42 03 905 A1 | 8/1993 |
| DE | 43 21 008 C1 | 5/1994 |
| DE | 43 19 805 A1 | 12/1994 |
| DE | 44 22 100 C1 | 12/1995 |
| DE | 195 20 913 A1 | 12/1996 |
| DE | 298 10 175 U1 | 8/1998 |
| DE | 198 24 057 C1 | 7/1999 |
| DE | 198 17 995 C1 | 9/1999 |
| DE | 199 24 513 C1 | 8/2000 |
| DE | 200 08 860 U1 | 9/2000 |
| DE | 199 29 327 A1 | 12/2000 |
| DE | 199 33 223 A1 | 1/2001 |
| DE | 100 47 849 C1 | 10/2001 |
| DE | 101 00 146 A1 | 7/2002 |
| DE | 101 28 278 C1 | 9/2002 |
| DE | 103 13 965 B3 | 10/2004 |
| DE | 10 2004 030 027 A1 | 1/2005 |
| EP | 0 092 528 A1 | 10/1983 |
| EP | 0 436 855 A1 | 7/1991 |
| EP | 0 543 283 A1 | 5/1993 |
| EP | 0 597 817 A2 | 5/1994 |
| EP | 0 622 086 A1 | 11/1994 |
| EP | 0 697 220 A1 | 2/1996 |
| EP | 0 701 827 A2 | 3/1996 |
| EP | 0 917 881 A2 | 5/1999 |
| EP | 0 952 433 A1 | 10/1999 |
| EP | 1 163 917 A1 | 12/2001 |
| EP | 1 234 590 A1 | 8/2002 |
| EP | 1 266 668 A1 | 12/2002 |
| EP | 1 297 857 A1 | 4/2003 |
| EP | 1 349 632 | 10/2003 |
| EP | 1 454 643 A1 | 9/2004 |
| EP | 1 514 563 A1 | 3/2005 |
| EP | 1 543 853 A1 | 6/2005 |
| ES | 1 040 983 U | 6/1999 |
| ES | 2 184 560 A1 | 4/2003 |
| FR | 2 700 121 A1 | 7/1994 |
| FR | 2 704 150 A1 | 10/1994 |
| GB | 1 292 730 A | 10/1972 |
| JP | 2001-224697 A | 8/2001 |
| JP | 2002-126471 A | 5/2002 |
| JP | 2004-329265 A | 11/2004 |
| JP | 2005-283342 A | 10/2005 |
| WO | 96/09080 A1 | 3/1996 |
| WO | 96/25214 A1 | 8/1996 |
| WO | 96/40313 A1 | 12/1996 |
| WO | 00/74833 A1 | 12/2000 |
| WO | 02/45813 A1 | 6/2002 |
| WO | 2004/064886 A2 | 8/2004 |
| WO | 2005/014083 A1 | 2/2005 |
| WO | 2005/021067 A1 | 3/2005 |
| WO | 2005/025726 A2 | 3/2005 |

* cited by examiner

DEVICE FOR CONNECTING TO A LIQUID SOURCE

BACKGROUND OF THE INVENTION

The present invention relates to a connecting device to a source of a liquid.

Specifically, though not exclusively, the invention can be usefully applied in connecting a medical apparatus, for example a dialysis apparatus, to a centralised supply plant of a medical liquid, for example a dialysis liquid.

As known, a centralised supply plant of liquid for dialysis is connected to a plurality of remote dialysis stations by means of a distribution circuit. One of the problems connected to this type of plant is protection against the risk of back-contamination of the whole distribution circuit due to a malfunctioning of a dialysis station in which, for example, a chemical disinfection process is under way: in this case, the propagation of the disinfectant in the distribution circuit would represent an enormous risk for the safety of the patients subject to treatment in the other dialysis stations.

US Patent Publication No. US 2005/0047959 describes a connecting device for connecting a medical apparatus (for example a dialysis machine or a inverse osmosis system) with a supply system of a cleaning or disinfecting agent. The connecting device comprises a buffer chamber or storage chamber, a connection line connecting the upper part of the buffer chamber with the medical apparatus, a siphon connecting the lower part of the buffer chamber with a source of the cleaning or disinfecting agent, and a vent line which connects the upper part of the buffer chamber with the external environment. The connecting line is provided with a pump for moving the cleaning or disinfecting agent and a closure valve. The buffer chamber is provided with a liquid sensor arranged at a level which is lower with respect to the top of the siphon and is superior with respect to the mouth of the siphon in the buffer chamber. The vent line is provided with a vent valve. During the washing and disinfecting procedure of the medical apparatus the closure valve is opened, the pump activated, while the vent valve is closed. During the other phases of the medical apparatus the closure valve is closed, the pump still, and the vent valve is open. The siphon ensures that at the end of the washing and disinfecting procedure, the buffer chamber is emptied of liquid. Further, the connecting device provides a security system which is able to detect if, beyond the procedure of washing and disinfecting, there are liquid leaks passing from the medical apparatus to the buffer chamber through the closure valve. The device serves to reduce the risk of contaminating the medical apparatus with the washing and disinfecting liquid when not in the stage of washing and disinfecting (for example during a medical treatment of a patient), as well as the risk of altering the washing and disinfecting liquid in a controlled way with medical fluid coming from the medical apparatus. In this way it is possible to keep the washing and disinfecting liquid constantly connected to the medical apparatus.

U.S. Pat. No. 5,015,389 describes a system for distribution of bicarbonate concentrate to a plurality of remote hemodialysis units, in which the bicarbonate concentrate is kept in continuous re-circulation along a ring-shaped distribution line, even in the presence of variations in the flow demand for the concentrate by the various hemodialysis units.

FR 2704150 discloses a plurality of dialysis machines connected to a central water purification unit by means of a supply ring which starts from the above-mentioned central unit and returns to the same unit. Each dialysis machine is provided with a connector for connecting the above-mentioned supply ring in order to ensure a continuous circulation of water along the ring and the taking of the necessary delivery of water for the functioning of the dialysis machine. Each connector is configured for connecting to a respective counter-connector which is predisposed along the supply ring. Each counter-connector is normally closed and is opened by effect of the mechanical interaction with a projection on the connector, predisposed on the dialysis machine. Each connector is provided with a solenoid to enable the water supplied to the supply ring to enter the dialysis circuit of the single dialysis machine.

DE 10047849 C1 describes a pure water distribution system, the water being prepared by an inverse osmosis plant, in which a ring-closed circuit supplies pure water to a plurality of dialysis machines. The same ring-closed circuit can be used to distribute the cleaning liquid to the various dialysis machines during the non-treatment stage (service stage) of the machines, in general during the night-time. Each dialysis machine is provided with a valve enabling ingress of the cleaning liquid coming from the distribution circuit. Further, the distribution circuit is provided with one or more temperature sensors connected to the control unit of each dialysis machine. The above-mentioned valve is opened by the control unit of the dialysis machine only when the temperature of the cleaning liquid, measured by the above-said sensor, has exceeded a predetermined suitable threshold.

EP 701827 describes a dialysis machine connected to a source of water via a control valve having two inlet ports, one for the water and another for the chemical disinfectant, and at least an outlet port which is connected to the intake of a pump and which is selectively placed in communication with one or the other of the inlet ports by means of a mobile obturator.

U.S. Pat. No. 5,256,371 describes a device for connecting a dialysis circuit of a dialysis machine to an external liquid source, in which the source normally comprises a water supply connection and a water discharge connection predisposed on the clinic's wall. The connecting device comprises an inlet line, an outlet line, a bypass line, and five valves arranged on the bypass line, two on the outlet line before and after the bypass line, and the other two on the inlet line before and after the bypass line. U.S. Pat. No. 5,256,371 further describes a method which uses the above-said connecting device for complete disinfection of both the dialysis machine and the above-mentioned connections fixed to the clinic's wall.

EP 622086 describes a connection of a dialysis machine to an external liquid source, the connection being provided with a safety device comprising two valves arranged in series along the connecting line, a pump for pressurising the intermediate tract of line comprised between the two valves, a pressure sensor operating between the two valves, and a control unit which performs a check on the integrity of the valves by monitoring the pressure in the intermediate tract of line.

SUMMARY OF THE INVENTION

An aim of the present invention is to provide a connecting device which can connect, in safe conditions, a medical apparatus to a liquid source.

A further aim of the invention is to realise a medical system in which a centralised source of a liquid can be connected in safe conditions to a plurality of remote medical apparatus.

A further aim is to provide an apparatus for extracorporeal blood treatment which can be connected in safe conditions to a centralised source of an operating liquid.

An advantage of the invention is to provide a connecting device which is constructionally simple and economical and considerably reliable, and which ensures against the risk of back-contamination on the part of a contaminating agent (for example a disinfectant liquid and/or a cleaning liquid) which, coming from a medical apparatus, can spread to a fluid distribution system to which the apparatus is connected.

A still further advantage is represented by the fact that the connecting device can provide the desired degree of safety by means of a monitoring system which uses sensors (for example liquid level sensors or liquid/air presence sensors) of relatively low-cost and highly reliable.

The device of the invention can usefully operate in a system for distributing an operating liquid to various medical work stations. The device is for protecting the distribution system from contamination by a contaminating liquid in the case of a malfunctioning of one of the work stations using the contaminating liquid (this is the case, for example, of a work station which is performing a chemical disinfection treatment).

These aims and others besides are all attained by the present invention, as it is characterised in one or more of the appended claims.

In a specific embodiment of the invention, the connecting device is able to generate a safety barrier constituted by a volume of air internally of a buffer chamber.

In a specific embodiment of the invention, the connecting device comprises a buffer chamber able to generate a volume of air which interrupts a liquid communication between two zones of a liquid transport line, and a monitoring system of any leaking of liquid entering into the volume of air defined in the buffer chamber. This monitoring system can comprise one or more means for detecting the presence/absence of liquid/air in the above-mentioned buffer chamber.

In a specific embodiment of the invention, the monitoring system comprises one or more liquid level sensors (for example a series of three or four or even more sensors distributed to operate at various levels in the buffer chamber) or other sensor systems for identifying the quantity of liquid/air present in the buffer chamber, and/or to detect the presence/absence of liquid/air in the buffer chamber or, at least, in a predetermined zone of the chamber itself.

Further characteristics and advantages of the present invention will better emerge from the detailed description that follows, of at least an embodiment of the invention, illustrated by way of non-limiting example in the accompanying figures of the drawings.

BRIEF DESCRIPTION OF THE DRAWINGS

The description will be made herein below with reference to the accompanying figures of the drawings, provided by way of non-limiting example, in which.

DETAILED DESCRIPTION

Figure 1:
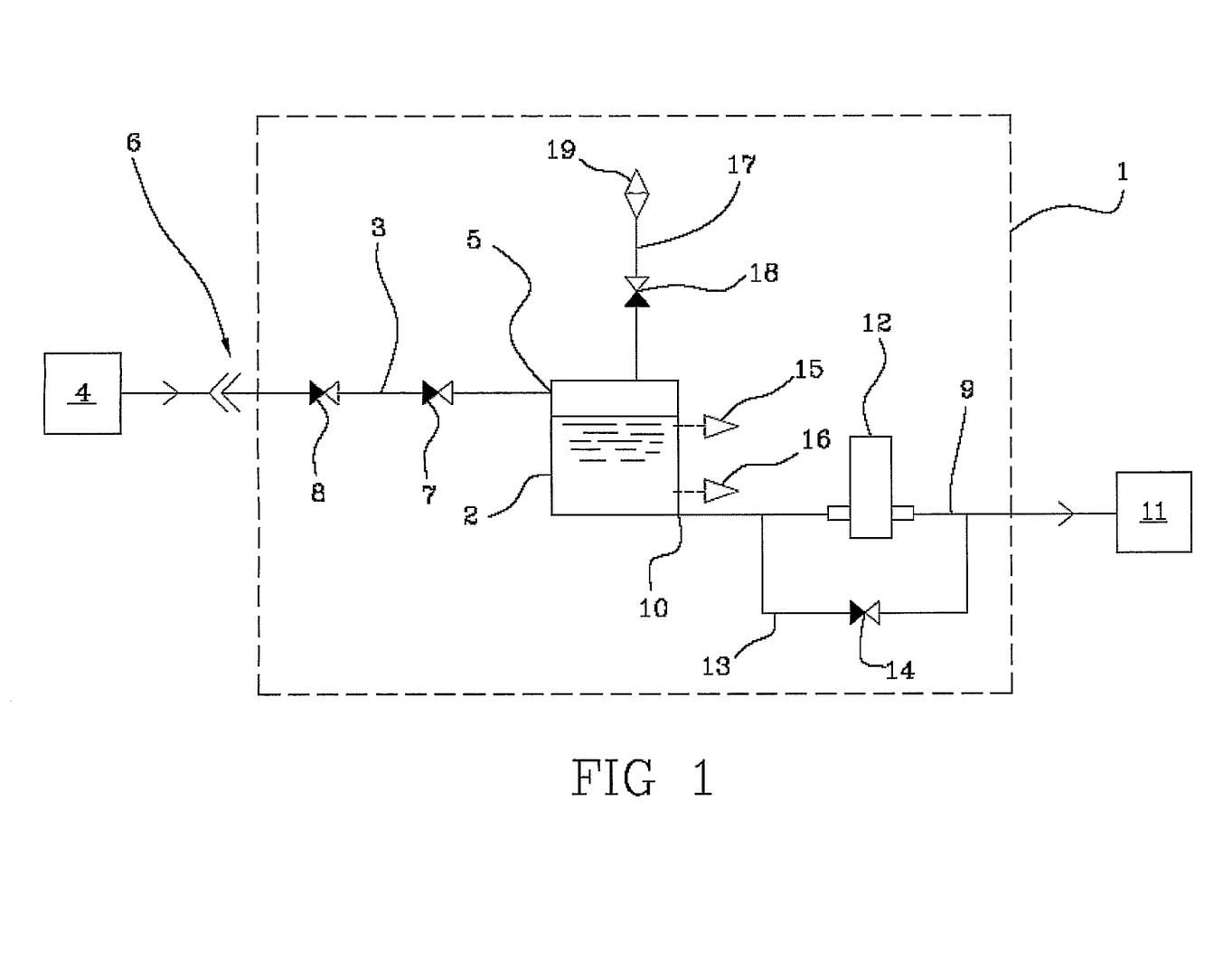
FIG. 1 is an embodiment of a connecting device between a medical apparatus and a source of a liquid, made according to the present invention.

With reference to FIG. 1, 1 denotes in its entirety a connecting device of a medical treatment apparatus (schematically illustrated and denoted by 11) to a liquid source (schematically illustrated and indicated by 4). The connecting device 1 comprises a buffer chamber 2 having at least a fluid passage section which is greater than the fluid transport lines which lead from the chamber itself. The buffer chamber 2 defines substantially a widening of section along a fluid transport line; at the section-widening the flow slows down. The buffer chamber 2 is extended in height in order to define at least an upper part and at least a lower part. The buffer chamber 2 is predisposed to generate an air barrier which interrupts two consecutive tracts of a fluid transport line. The buffer chamber 2 forms an air gap which functions as a safety element against undesired passage of liquid (in one direction and/or in the other) at determined operative stages in which it is necessary to guarantee separation or isolation between the medical apparatus and the liquid source, which source can be used by the medical apparatus in other operative stages for liquid supply. In substance, the buffer chamber 2 serves to ensure than in some predetermined operating stages in which the passage of liquid is undesired, the passage of liquid is effectively stopped. The above guarantee is given by verification of the presence of air, or in any case of a sufficient quantity of air in the buffer chamber 2 itself during the operating stages which require separation or isolation.

The device 1 comprises a first connecting line 3 having a first end which is connectable to a liquid source 4 and a second end connected to an inlet 5 arranged in an upper zone of the buffer chamber 2. The first end of the first connecting line 3 can be connected to the liquid source 4 in a fixed connection or, as in the illustrated embodiment, via any known type of removable connection 6. A first valve 7 and a second valve 8 are arranged in series on the first connecting line 3. The first valve 7, as well as the second valve 8, is in the specific case an on-off valve (for example a solenoid) commanded by a control unit (not illustrated).

The connecting device 1 comprises a second connecting line 9 having a first end connected to an outlet 10 arranged in a lower zone of the buffer chamber 2 and a second end connectable to the medical treatment device 11. The second end of the second connecting line 9 can be connected to the medical treatment device 11 in a fixed way, as in the illustrated embodiment, or via any known type of removable connection. The outlet 10 is arranged at a lower level than the inlet 5. A liquid moving pump 12 is predisposed on the second connecting line 9 to transport the fluid. The liquid moving pump 12 is of the reversible type, i.e. it can move the liquid in one direction or another. The liquid moving pump 12 is, in the specific embodiment, a positive displacement pump, for example with a rotary and oscillating piston. It would however be possible to use any type of known pump, in particular a volumetric pump or any other type of pump of system for fluid movement along a line or a circuit for fluid transport. The second connecting line 9 is provided with a bypass line 13 for bypassing the liquid moving pump 12. The bypass line 13 is provided with a bypass valve (for example an on-off valve) which is commanded by the control unit (the bypass valve can be, for example, a solenoid).

The connecting device 1 is provided with a liquid/air detector operating in the buffer chamber 2 between the inlet 5 and the outlet 10. The liquid/air detector can comprise any sensor or system of sensors able to provide a signal indicating the presence or not of gas (air) in the buffer chamber 2 or in any case the presence of a determined quantity of gas (air) internally of the buffer chamber 2 itself. The liquid/air sensor can comprise, for example, a moisture sensor (the absence of moisture, or presence of a quantity of moisture which is below a predetermined threshold being indicative of the presence of air), or a pressure sensor for volumetric measuring of gas (the pressure signal being processable in such a way as to determine the volume of air present in the buffer chamber 2, for example on the basis of the equation of state of an ideal gas and the knowledge of the volume of the buffer chamber 2, as well as possibly the temperature), or any known type of liquid level sensor (of the YES/NO type) or liquid level measuring device (which provides a signal indicating the level), such as for example a sensor or ultrasound-type level measuring device, or other acoustic signal, or optical, or mechanical (for example a float-type device) or any other type. In the specific embodiment the liquid/air detector comprises a first and a second liquid level sensor, respectively 15 and 16, for example of the optic type, arranged at two different levels (one above the other) and configured to signal the presence of liquid in the buffer chamber 2 at a first and, respectively a second liquid level, both levels being intermediate between the inlet 5 level and the outlet 10 level of the buffer chamber 2. As already mentioned, the upper level sensor 15 operates at a lower level than the inlet 5 of the buffer chamber 2. The lower level sensor 16 operates at a higher level than the outlet 10 level of the buffer chamber 2.

The connecting device 1 further comprises a vent line 17 connected to an upper zone of the buffer chamber 2 and provided with a vent valve 18, for example a solenoid or another type of valve activated on command by the control unit. The vent line 17 is further provided with one or more air filters 19 (for example hydrophobic membrane filters) for communication with the outside environment.

The control unit of the connecting device 1 is connected to the liquid/air detector (i.e., in the specific embodiment, the two level sensors 15 and 16), to the first valve 7 and second valve 8 of the two first connecting lines 3, to the liquid moving pump 12 of the second connecting line 9 and to the vent valve 18 on the vent line 17. The control unit is further connected to the medical treatment device 11 (it can, for example, be a control unit of the device 11 itself).

The control unit is programmed to perform a safety control procedure which comprises the following operations:
  a) Receiving data from the outside to recognise whether the medical treatment device 11 is in a mode requiring the separation or isolation of the liquid source 4, such as for example a disinfecting mode and/or a washing mode;
  b) Closing both the first valve 7 and (if present) the second valve 8 when it is recognised that the medical treatment device 11 is in a disinfecting mode and/or a washing mode or in any other mode which requires, for example for reasons of safety, the isolation or separation of the medical treatment device 11 from the liquid source 4;
  c) Signalling an anomalous situation (the signal can comprise, for example, one or more from the following operations: an acoustic or visual signal 9, an on-screen message on the user interface of the medical apparatus 11, an automatic interruption of one or more functions underway by the medical apparatus 11, any operating mode known for placing the medical apparatus 11 in a safe situation etc.) if, while the medical apparatus 11 is in the mode requiring isolation/separation (for example disinfection/washing), the liquid/air detector of the liquid detects liquid in the buffer chamber 2 above a predetermined level (or in any case it detects a quantity of liquid above a certain threshold and/or a quantity of air below a certain threshold).

The above-mentioned safety control procedure can further include the control unit's being programmed to open the vent valve 18 in a case in which the medical apparatus 11 is recognised to be in a disinfecting and/or washing mode or in another mode requiring isolation/separation.

The above-described safety control procedure has the function of ensuring that between the medical apparatus 11 and the liquid source 4 there is a safety barrier, represented by a volume of air, in the present embodiment a buffer chamber 2 full of air. As mentioned, the safety barrier must be ensured during certain operating stages of the medical apparatus 11 in which the medical apparatus 11 has to be absolutely separate (that is, not in liquid communication) with respect to the liquid source 4, (in the present embodiment one of the operative stages consists if the procedure of disinfection and/or washing). This ensures, in particular, that the disinfecting and/or washing liquid circulating in the medical apparatus 11 does not pass into circulation towards the liquid source 4. This guarantee is of fundamental importance when, for example, the liquid source 4 is in communication with other medical apparatus: consider a case in which the liquid source 4 comprises or is part of a centralised plant distributing a liquid to a multiplicity of remote medical apparatus. In this case the safety control procedure guarantees, for example, that while the medical apparatus 11 is performing a disinfection and/or washing procedure, there is no risk that the disinfection and/or washing liquid can be supplied, by error, to a patient who is contemporaneously subjected to a treatment by a further medical apparatus which is also connected to the same centralised distribution plant. In general the above-described control procedure prevents a dangerous situation in which, in a system comprising a centralised distribution plant of a liquid connected to a plurality of medical apparatus by means of a plurality of connecting devices such as the one described herein above, a second liquid used by a single medical apparatus might diffuse by error internally of the centralised plant. A typical case of a risky situation is, for example, when a first medical apparatus is performing a first procedure using the first liquid coming from the centralised distribution plant (for example a medical treatment using a medical liquid), while a second medical apparatus is performing a second procedure, which does not require the first liquid and which uses a second, dangerous liquid (for example the disinfecting and/or washing liquid of the apparatus) which, if introduced into the circuit of the first apparatus while performing the first procedure, could cause serious harm to the health of the patient and/or a pollution of the entire distribution network of the first liquid.

The control unit is further programmed to perform a valve integrity test comprising the following stages:
  a) activating the reversible liquid pump 12 to empty the buffer chamber 2 of liquid, in which the emptying stage is performed with the first valve 7 closed and the vent valve 18 open (the second valve 8, if present, can be closed too, or even left open, as will be explained in more detail herein below);
  b) activating the reversible liquid pump 12 in order to aspirate/pump fluid from/to the buffer chamber 2 after the first stage a) of emptying, in which the stage of aspiration/pumping is performed with the first valve 7 closed and the vent valve 18 also closed (in this stage too the second valve 8, if present, can be open or closed);
  c) check if, after stage b) of aspiration/pumping, the buffer chamber 2 is still empty of liquid, the check being performed by the level sensor system 15 and 16.

The above integrity test can be performed, as mentioned, in aspiration (depression of the buffer chamber 2); the liquid moving pump 12 is reversible and therefore can function in both directions. It has been observed however that the test performed in compression, where the liquid movement pump 12 is pumping towards the buffer chamber 2, seems to be more efficient.

The integrity test can be performed, as already mentioned, with the second valve 8 open, with the aim of checking the integrity of only the first valve 7, and then can be repeated to check the integrity of the second valve 8, this time keeping the first valve 7 open. This repetition therefore comprises the following stages:

a) Activating the reversible liquid pump 12 to further aspirate/pump from/to the buffer chamber 2 empty of liquid (full of air), in which this stage of further aspiration/pumping is performed with the second valve 8 closed, the vent valve 18 closed, and the first valve 7 open;

b) Checking if, after the stage of further aspiration/pumping, the buffer chamber 2 is still empty of liquid (i.e. substantially full of air).

In an embodiment of the invention which is not illustrated, more than one first connecting line 3 could depart from the buffer chamber 2, as well as and/or more than one second connecting line 9. In other words, the connecting device can comprise: one or more further first connecting lines, each of which has a first end which can be connected to one or more liquid sources (for example for supplying different liquids) and a second end connected to an inlet arranged in the upper zone of the buffer chamber; one or more further first valves (and possibly second valves) each of which is arranged in a respective line of the above-cited further first connecting lines; one or more further second connecting lines, each of which has a first end connected to an outlet arranged in the lower zone of the buffer chamber and a second connectable to one or more medical treatment apparatus; and one or more further liquid movement pumps, each of which is arranged in a respective line of the further second connecting lines. With this embodiment too the control unit can be programmed to perform the above-described safety control procedure and the above-cited valve integrity test.

The connecting device of the invention can be applied to a medical system comprising one or more medical apparatus connected to at least a liquid source via one or more of these connecting devices. The liquid source 4 can comprise, as previously mentioned, a centralised distribution plant of an operating liquid, in which the operating liquid can comprise one or more of the following liquids: a chemical disinfectant and/or a washing liquid for the disinfecting/cleaning of the fluid transport circuit of the medical apparatus, a hot disinfectant (water or another heated liquid, heated to a disinfecting temperature), a medical treatment fluid (for example a dialysis fluid and/or a replacement fluid for performing a hemodialysis and/or hemo(dia)filtration treatment), a fluid containing one or more components of a treatment fluid (for example a solution—concentrated—of bicarbonate, or sodium chloride, or a mixture of one or more salts for a hemodialysis or hemo(dia)filtration, such as for example sodium, magnesium, potassium, calcium, glucose, etc.) an infusion fluid etc. The medical apparatus of the above-described medical system can comprise one or more extracorporeal blood treatment, such as for example a hemodialysis apparatus, a hemo(dia)filtration apparatus, a hemoperfusion apparatus, a plasmapheresis apparatus, a therapeutic plasma exchange, an apparatus for treatment of hepatic insufficiency, etc.

Figure 2:
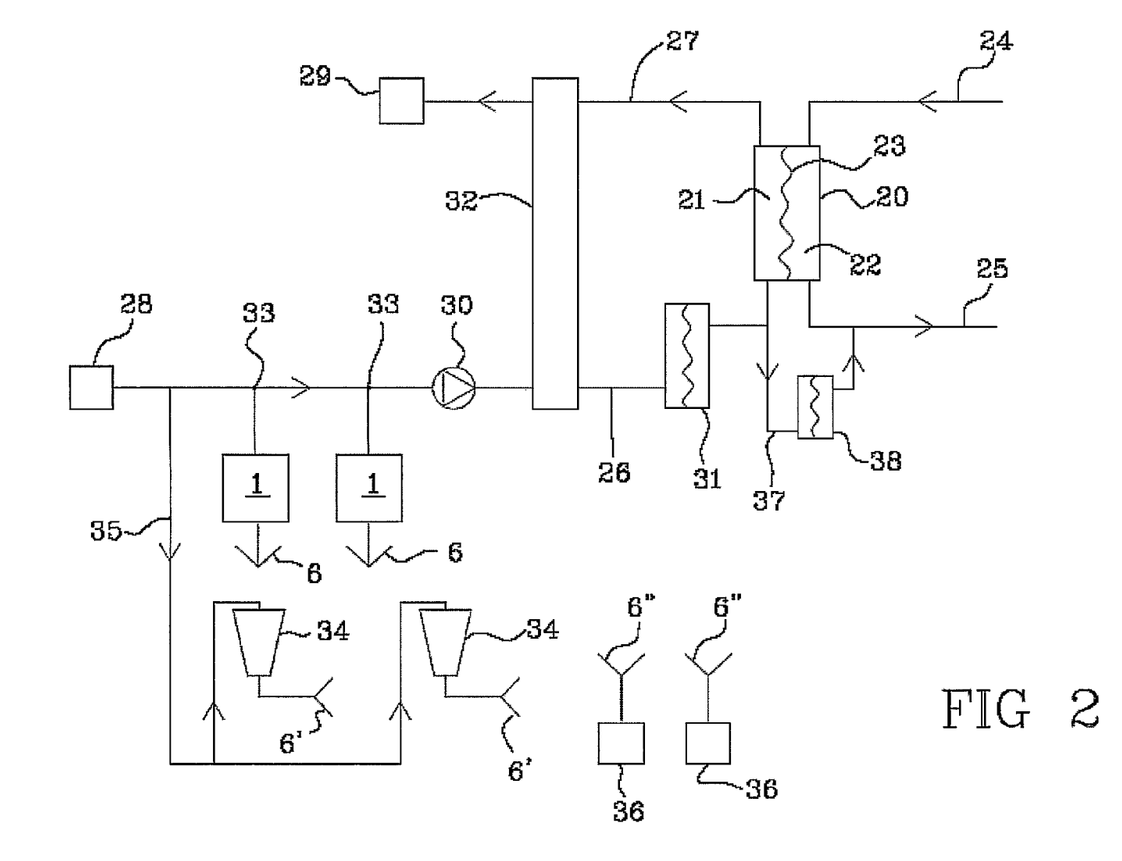
FIG. 2 is a first embodiment of an apparatus for extracorporeal blood treatment which uses the connecting device of FIG. 1.
Figure 3:
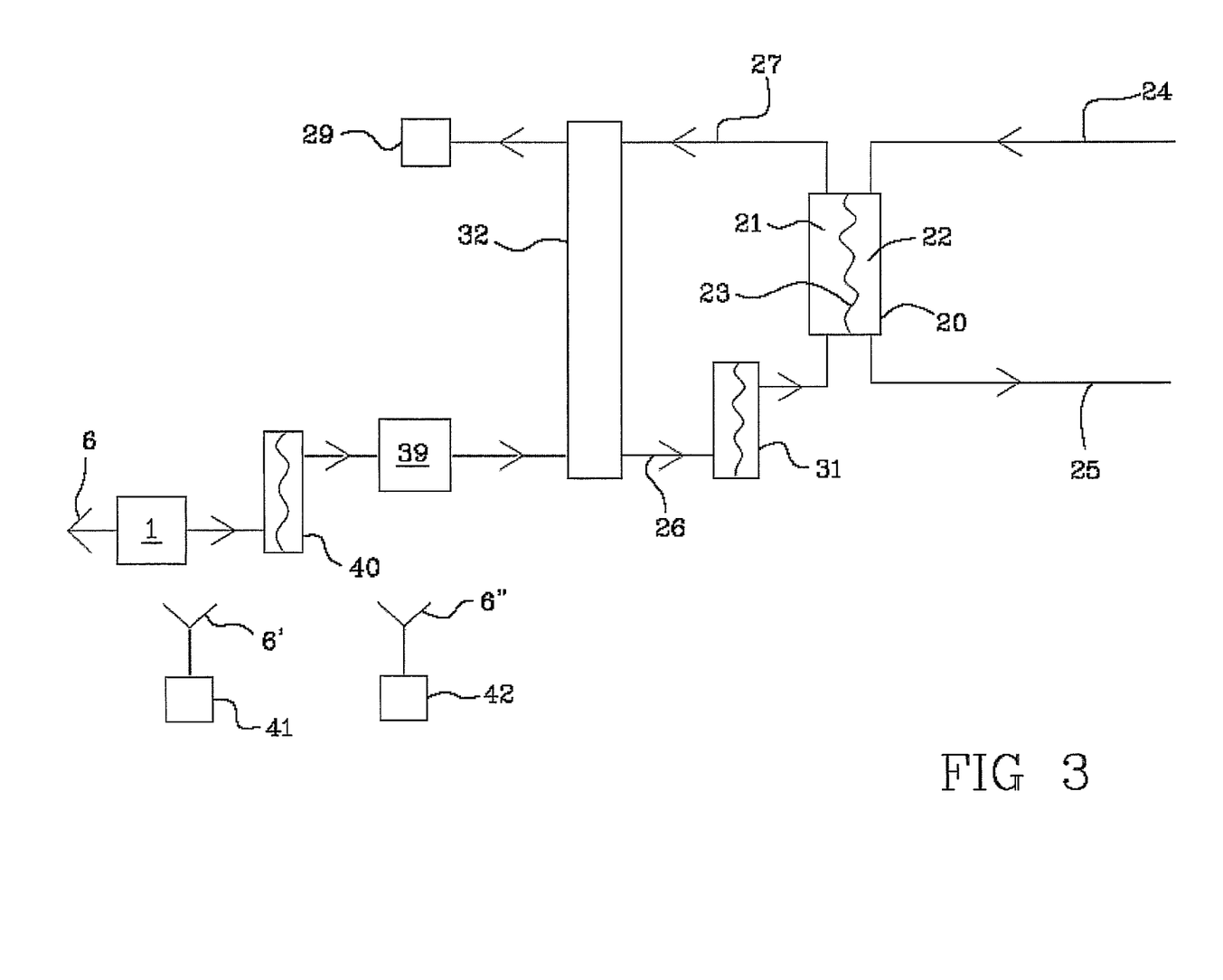
FIG. 3 is a second embodiment of an apparatus for extracorporeal blood treatment which uses the connecting device of FIG. 1.

FIGS. 2 and 3 illustrate two examples of how the connecting device 1 can be connected to an apparatus for extracorporeal blood treatment. The elements which are the same in FIGS. 2 and 3 have been denoted using the same numbers, for the sake of simplicity.

The extracorporeal blood treatment apparatus of FIG. 2 comprises a membrane device 20 for extracorporeal blood treatment which in turn comprises a first chamber 21 and a second chamber 22 separated by a semipermeable membrane 23. The apparatus comprises an extracorporeal blood circuit connected to the second chamber 22 (blood chamber) of the membrane device 20. The extracorporeal blood circuit can comprise any one of the blood circuits of known type which are usable in a dialysis apparatus and/or a hemo(dia)filtration apparatus. The extracorporeal blood circuit in FIG. 2 has been schematically represented as an arterial line 24 for blood removal from the patient and in a venous line 25 of return of blood to the patient. The apparatus further comprises a fluid circuit comprising a fresh treatment fluid supply line 26 connected to an inlet of the first chamber 21, and a used treatment fluid discharge line 27 connected to an outlet of the first chamber 21. The fresh treatment fluid supply line 26 further has an inlet end connected to a water source 28. The used treatment fluid discharge line 27 further has a discharge end connected to a drainage 29. The fluid circuit is provided with at least a fluid movement pump 30 along the circuit itself and a first ultrafilter 31 for reducing the quantity of bacteria and/or endotoxins in the treatment fluid upstream of the membrane device. The apparatus further comprises a fluid balancing system 32 for controlling the flow balance in the fresh treatment fluid supply line 26 and the used treatment fluid discharge line 27 before and after the membrane device 20. The fluid balancing system 32 can comprise anyone of the known balancing systems used in hemodialysis apparatus (volumetric balancing chamber system, two flow-meter system, differential flow-meter system, scale system etc.). The apparatus further comprises at least a connecting device 1 such as the one described above (in the specific case it comprises two, as will be explained in more detail herein below). The second end of the second connecting line of each connecting device 1 is connected to the fluid circuit. In particular the second end branches, for each device, from a respective branch point 33 of the fresh treatment fluid supply line 26. Each of the branch points 33 is in a zone arranged upstream of the fluid balancing system 32. In the specific example, in which there are two connecting devices 1, both have the second end of the second connecting line which branches from two branch points 33 arranged on the fresh treatment fluid supply line upstream of the fluid balancing system 32. The two connecting devices 1 are inserted in an on-line preparation system of a fresh fluid treatment starting from water and concentrates. In particular the preparation system can comprise any one of the known systems for on-line preparation of a dialysis fluid starting from water and concentrates. In the specific case the preparation system comprises at least two concentrate containers 34 which receive water from the water source 28 via a branch line 35 which branches from the main supply line fresh treatment fluid supply line 26. The preparation system can include a third concentrate container (not illustrated). The water coming from the source 28 (possibly heated and degassed) is mixed, in a known way, with the concentrates contained in the containers 34 to give rise to a concentrated solution which is introduced into the fresh treatment fluid supply line 26 to form, finally, the fresh treatment fluid to be sent to the first chamber 21 of the membrane device 20 and/or the extracorporeal blood circuit. Sensors are included (of known type and not illustrated, such as for example electrical conductivity sensors, temperature sensors, pH sensors) to check that the fresh treatment fluid possesses the desired characteristics (in particular the temperature and chemical composition). The treatment fluid preparation system, being substantially of known type, is not described in further detail. Of importance is the fact that the connecting devices 1 enable selective connection with the concentrate containers 34 or with two sources of concentrate solution 36 which are part of a centralised distribution system. The selective connection can be performed manually by means of the connections 6 and the corresponding removable counter-connections 6' and 6'', which both the concentrate lines connected to the concentrate containers 34 and the concentrate lines connected to the sources 36 which are part of the centralised system distribution are equipped with. The connecting devices 1 ensure that even in a case where the counter-connections 6" of the concentrate solution 36 sources belonging to the centralised distribution system are not removed but remain coupled to the removable connections 6 of the connecting devices, there is no risk of the polluting fluid's passing from the extracorporeal blood apparatus to the centralised distribution system (and vice versa).

In the specific case of FIG. 2, the extracorporeal blood treatment apparatus is a hemodiafiltration apparatus comprising a replacement fluid supply line 37 provided with a second ultrafilter 38. In the specific case of FIG. 2 a hemodiafiltration apparatus in post-dilution is illustrated, although it would be possible with the apparatus in pre-dilution, or in pre- and post-dilution. The application can also be used in a hemodialysis apparatus, or in a hemofiltration apparatus, in which case the connecting device or devices can be connected to the replacement fluid supply line 37. It is also possible, in a hemodiafiltration apparatus, for one or more connecting devices 1 to be connected to the dialysis fluid supply line (as in FIG. 2) and/or the replacement fluid supply line.

With reference to the hemodialysis apparatus of FIG. 3, the same elements that appeared in FIG. 2 have been denoted using the same numbers, and will not be further described. The fresh treatment fluid supply line 26 is provided with a device for on-line preparation of the fluid 39 starting from water and concentrates. The preparation device 39 can be any known device used in a machine for hemodialysis and/or hemo(dia)filtration, or the preparation device described with reference to FIG. 2 and provided with one or more connecting devices 1. The fresh treatment fluid supply line 26 has an inlet end which is provided with the connecting device 1. The fresh treatment fluid supply line 26 further has an ultrafilter 40 for reducing the quantity of bacteria and/or endotoxins in the flow arranged between the connecting device 1 and the on-line preparation device 39. The first end of the first connecting line 3 of the connecting device 1 is destined, in the specific case, to connection with a source of purified water 41 supplied by a centralised plant for production and distribution of purified water to a multiplicity of remote medical apparatus. The source of purified water 41 can comprise, for example, an inverse osmosis system. The source of purified water 41 is provided with an end for connecting to the connecting device 1 by means of a counter-connector 6' removably connectable with a corresponding connector 6 which the first end of the first connecting line 3 is provided. The connecting device 1 can be connectable (selectively) with a further source of liquid 42 provided with a corresponding counter-connector 6". The further source of liquid 42 can comprise, for example, a supply of a disinfecting fluid, a thermal and/or chemical liquid, which can originate from a centralised fluid production and distribution plant. The further source of liquid 42 can comprise, in a further example, a supply of a treatment fluid (for example a dialysis and/or a replacement fluid) which can operate in cooperation or alternatively to the preparation device 39 and which can be sourced from a centralised fluid production and distribution plant. In each case, the connecting device 1 provides a guarantee against risk of back-contamination of the sources 41 and 42 or of the extracorporeal blood treatment apparatus, in determined operative stages of the sources 41 and 42 or the extracorporeal blood treatment apparatus, where the latter must be isolated from the sources 41 and 42. The hemodialysis apparatus of FIG. 3 can be provided with a pre-dilution line and/or a post-dilution line in order for a hemo(dia)filtration treatment to be performed.

Also in the case of FIG. 2 and line 3, the functioning of the connecting device 1 is how it is described with reference to FIG. 1. The liquid movement pump 12 is activated to supply the medical apparatus with operating liquid in the operating modes which include use of the liquid (for example in patient treatment mode when the operating liquid is a treatment liquid), with the first valve 7 and the second valve 8 open; in this situation at least the lower level sensor 16 will detect liquid. When a mode not requiring the treatment liquid is selected or intervenes automatically, but instead demands isolation of the medical apparatus from the operating liquid source (for example a disinfecting mode), the first valve 7 and the second valve 8 will be closed and the liquid movement pump 12 will be activated to empty the buffer chamber 2 (with the vent valve 18 open) until the two level sensors 15 and 16 both detect air. In this situation, between the medical apparatus and the centralised system of distribution an air spacer is interposed, which functions as a safety barrier. The valve integrity test comprises closure of a valve on the first connecting line 3 (for example the first valve 7) and the closure of the vent valve 18 (keeping the second valve 8 open, even if, as has been observed, it can be closed to perform a contemporary integrity test on both valves) and the activating of the liquid moving pump 12 in inverse direction for pumping towards the buffer chamber 2 (as has been observed, a test under aspiration conditions is also possible): if the first valve 7 and the vent valve 18 are in the correct sealedly closed position, the upper level sensor 15 and lower level sensor 16 should in all cases detect the presence of air. The valve integrity test is repeated for the second valve 8 which is closed, while the first valve 7 is opened and the vent valve 18 is kept closed; the pumping action towards (or aspiration from) the buffer chamber 2 is repeated and the integrity test is considered to have been concluded with success if this time too the upper and lower level sensors 16 both detect air.

The connecting device 1 associated to the apparatus of FIGS. 2 and 3 can comprise any one of the connecting devices 1 described in the claims that follow relative to a connecting device. The functioning of the devices is the same and directly deducible from what is stated with reference to the functioning of the device of FIG. 1.

| Legend | |
|---|---|
| 1 | Connecting device of a medical treatment apparatus to a source of a liquid |
| 2 | buffer chamber |
| 3 | first connecting line |
| 4 | liquid source |
| 5 | buffer chamber inlet |
| 6 | 6' 6" removable connections |
| 7 | first valve |
| 8 | second valve |
| 9 | second connecting line |
| 10 | buffer chamber outlet |
| 11 | medical treatment apparatus |
| 12 | reversible liquid pump |
| 13 | bypass line |
| 14 | bypass valve |
| 15 | first liquid level sensor |
| 16 | second liquid level sensor |
| 17 | vent line |
| 18 | vent valve |
| 19 | air filter |
| 20 | membrane device for extracorporeal blood treatment |
| 21 | first chamber of membrane device |
| 22 | second chamber of membrane device |

| Legend | |
|---|---|
| 23 | semipermeable membrane |
| 24 | arterial line |
| 25 | venous line |
| 26 | fresh treatment fluid supply line |
| 27 | used treatment fluid discharge line |
| 28 | water source |
| 29 | drainage |
| 30 | fluid moving pump |
| 31 | ultrafilter pump |
| 32 | fluid balancing system |
| 33 | branch point |
| 34 | concentrate containers |
| 35 | branch line |
| 36 | concentrate solution sources |
| 37 | replacement fluid supply line |
| 38 | second ultrafilter |
| 39 | device for on-line preparation of an operating fluid starting from water and concentrates |
| 40 | ultrafilter |
| 41 | purified water source |
| 42 | further liquid source |

The invention claimed is:

1. A connecting device of a medical apparatus to a liquid source, comprising:
 a buffer chamber having an upper zone, a lower zone, an inlet arranged in the upper zone, and an outlet arranged in the lower zone;
 a first connecting line having a first end which is connectable to the liquid source and a second end connected to said inlet;
 a second connecting line having a first end connected to said outlet and a second end connectable to the medical apparatus;
 a first valve arranged in the first connecting line;
 a pump arranged in the second connecting line;
 a liquid/gas detector operating in the buffer chamber, the liquid/gas detector comprising one or more sensors configured to provide a signal indicating the presence of liquid and/or gas, and
 a control unit connected to the liquid/gas detector, to the first valve and to the pump, the control unit being connectable to the medical apparatus and being programmed to perform following operations:
  receiving data for recognising whether the medical apparatus is in a predetermined operating mode;
  closing the first valve if the medical apparatus is in the predetermined operating mode;
  signalling an anomalous situation if, while the medical apparatus is in the predetermined operating mode, the liquid/gas detector finds liquid in the buffer chamber above a predetermined level.

2. The device of claim 1, wherein the liquid/gas detector operates at least between the inlet and the outlet.

3. The device of claim 1, wherein the liquid/gas detector comprises a first level sensor which is configured to signal a presence and a first level of liquid in the buffer chamber, the first level being intermediate between a level of said inlet and a level of said outlet.

4. The device of claim 3, wherein the liquid/gas detector comprises a second level sensor configured to signal a presence and a second level of liquid in the buffer chamber, the second level being intermediate between the level of said inlet and the level of said outlet, the second level being different from the first level.

5. The device of claim 1, wherein the one or more sensors are selected from a group of sensors which includes: a moisture sensor, a pressure sensor for volumetric measurement of gas, a level sensor or level measure of acoustic type, an ultrasound liquid level sensor, a level sensor or level measure of optic type, a level sensor or level measure of mechanical type, a float liquid level sensor, and a combination of one or more of the aforementioned sensors.

6. The device of claim 1, comprising a second valve arranged in series with the first valve along the first connecting line.

7. The device of claim 1, comprising a vent valve connected to the buffer chamber.

8. The device of claim 1, wherein the buffer chamber is connected to a vent valve which in turn is connected to the control unit, and wherein the control unit is programmed to open the vent valve if the medical apparatus is found to be in the predetermined operating mode.

9. The device of claim 1, comprising:
 a vent valve connected to the buffer chamber;
 wherein the control unit is programmed to perform a valve integrity test comprising following stages:
  activating the pump to empty the buffer chamber of liquid, the emptying stage being performed with the first valve closed and the vent valve open;
  activating the pump to either aspirate fluid from the buffer chamber or to pump fluid to the buffer chamber after the emptying stage, the aspiration/pumping stage being performed with the first valve closed and the vent valve closed;
  checking whether, after the aspiration/pumping stage, the buffer chamber is still empty of liquid.

10. The device of claim 9, comprising a second valve arranged in series with the first valve along the first connecting line; the stage of aspiration/pumping being performed with the second valve open; the valve integrity test further comprising stages of:
 activating the pump to further aspirate/pump fluid from/to the buffer chamber empty of liquid, the further aspiration/pumping stage being performed with the second valve closed, the vent valve closed and the first valve open;
 checking whether, after the further aspiration/pumping stage, the buffer chamber is still empty of liquid.

11. The device of claim 1, comprising:
 one or more further first connecting lines, each of which has a first end which is connectable to a liquid source and a second end connected to an inlet positioned in an upper zone of the buffer chamber;
 one or more further first valves, each of which is arranged in a respective one of the further first connecting lines.

12. The device of claim 1, comprising:
 one or more further second connecting lines, each of which has a first end connected to an outlet arranged in a lower zone of the buffer chamber and a second end which is connectable to the medical treatment apparatus;
 one or more further pumps, each of which is arranged in a respective one of the further second connection lines.

13. A medical system comprising:
 at least a medical apparatus;
 at least a liquid source;
 at least a connecting device made according to claim 1 and configured for connecting the medical apparatus with the liquid source.

14. The medical system of claim 13, wherein the liquid source comprises a centralized distribution plant of an operating liquid to a plurality of medical apparatus.

15. The medical system of claim 14, wherein the operating liquid comprises one or more liquids selected from a group of liquids which includes: a chemical disinfectant, a cleaning liquid, a thermal disinfectant, a medical treatment fluid, a fluid for hemodialysis or hemo(dia)filtration, a fluid containing one or more components of a fluid for hemodialysis or hemo(dia)filtration, an infusion fluid, purified water, a inverse-osmosis-treated fluid.

16. The medical system of claim 13, wherein the medical apparatus comprises one or more medical apparatus selected from a group which includes: an extracorporeal blood treatment apparatus, a hemodialysis apparatus, a hemo(dia)filtration apparatus, a hemoperfusion apparatus, a plasmapheresis apparatus, a therapeutic plasma exchange apparatus, a renal insufficiency treatment apparatus.

17. An apparatus for extracorporeal blood treatment comprising:
   a membrane device for extracorporeal blood treatment, comprising a first chamber and a second chamber, separated from one another by a semipermeable membrane;
   a fluid circuit comprising a fresh treatment fluid line connected to an inlet of the first chamber, and a used treatment fluid line connected to an outlet of the first chamber;
   at least a fluid movement pump along the fluid circuit;
   a fluid balancing system for controlling a balance of flows in the fresh treatment fluid line and in the used fluid treatment line;
   at least a connecting device of claim 1, the second end of the second connecting line of the connecting device being connected to the fluid circuit.

18. The apparatus of claim 17, wherein the second end of the second connecting line of the connecting device is connected in a branch relationship with the fresh treatment fluid line.

19. The apparatus of claim 17, wherein the second end of the second connecting line of the connecting device is connected to a branch point of the fluid circuit arranged upstream of the fluid balancing system.

20. The apparatus of claim 17, comprising one or more further connecting devices, each comprising:
   a buffer chamber having an upper zone, a lower zone, an inlet arranged in the upper zone, and an outlet arranged in the lower zone;
   a first connecting line having a first end which is connectable to the liquid source and a second end connected to said inlet;
   a second connecting line having a first end connected to said outlet and a second end connectable to the medical apparatus;
   a first valve arranged in the first connecting line;
   a pump arranged in the second connecting line; and
   a liquid/gas detector operating in the buffer chamber, the liquid/gas detector comprising one or more sensors configured to provide a signal indicating the presence of liquid and/or gas, the second end of the second connecting line of each of the further connecting devices being connected to the fluid circuit.

21. The apparatus of claim 20, wherein the second end of the second connecting line of each of the further connecting devices is connected to a branch point of the fresh treatment fluid line positioned upstream of the fluid balancing system.

22. The apparatus of claim 17, configured to perform one or more of following treatments: hemodialysis, hemofiltration, hemodiafiltration, hemoperfusion, plasma exchange therapy, plasmapheresis, hepatic insufficiency treatment.

* * * * *

UNITED STATES PATENT AND TRADEMARK OFFICE
CERTIFICATE OF CORRECTION

PATENT NO. : 8,425,767 B2
APPLICATION NO. : 12/601191
DATED : April 23, 2013
INVENTOR(S) : Fava et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this
Eighth Day of September, 2015

Michelle K. Lee
*Director of the United States Patent and Trademark Office*